(12) United States Patent
Mueller (10) Patent No.: US 12,144,991 B2
(45) Date of Patent: Nov. 19, 2024

(54) METHOD FOR STIMULATING A TISSUE STRUCTURE BY MEANS OF AN ELECTRIC FIELD STRENGTH, A SYSTEM FOR STIMULATING A TISSUE STRUCTURE AND A MAGNETIC STRUCTURE FOR IMPLANTATION ON A TISSUE STRUCTURE

(71) Applicant: FRAUNHOFER-GESELLSCHAFT ZUR FÖRDERUNG DER ANGEWANDTEN FORSCHUNG E.V., Munich (DE)

(72) Inventor: Carsten Mueller, Wuerzburg (DE)

(73) Assignee: Fraunhofer-Gesellschaft zur Förderung der angewandten Forschung e.V.

( * ) Notice: Subject to any disclaimer, the term of this patent is extended or adjusted under 35 U.S.C. 154(b) by 1088 days.

(21) Appl. No.: 17/041,091

(22) PCT Filed: Mar. 28, 2019

(86) PCT No.: PCT/EP2019/057870
§ 371 (c)(1),
(2) Date: Sep. 24, 2020

(87) PCT Pub. No.: WO2019/185803
PCT Pub. Date: Oct. 3, 2019

(65) Prior Publication Data
US 2021/0106823 A1 Apr. 15, 2021

(30) Foreign Application Priority Data
Mar. 28, 2018 (DE) ..................... 10 2018 107 425.5

(51) Int. Cl.
*A61N 2/02* (2006.01)
*A61N 1/36* (2006.01)
(Continued)

(52) U.S. Cl.
CPC ............. *A61N 1/3605* (2013.01); *A61N 1/40* (2013.01); *A61N 2/02* (2013.01); *A61N 2/06* (2013.01)

(58) Field of Classification Search
CPC ................................................... A61N 2/00–12
See application file for complete search history.

(56) References Cited

U.S. PATENT DOCUMENTS

| 4,321,520 A | * | 3/1982 | Ueda | ......................... H02P 8/02 318/647 |
| 5,193,540 A | | 3/1993 | Schulman et al. | |

(Continued)

FOREIGN PATENT DOCUMENTS

| DE | 10208391 A1 | 9/2003 |
| DE | 102005062746 A1 | 7/2007 |

(Continued)

*Primary Examiner* — Thaddeus B Cox
(74) *Attorney, Agent, or Firm* — 2SPL Patent Attorneys PartG mbB; Kieran O'Leary (57) ABSTRACT

The subject matter of the application comprises a method for stimulating a tissue structure by means of an electric field strength. According to the method, an electromagnetic alternating field is generated in an environment of the tissue structure and the electromagnetic alternating field in the tissue structure is concentrated by means of an implanted magnetic structure within the environment. Further examples relate to a system for stimulating a tissue structure by means of an electric field strength with a portable coil device and a magnetic structure implantable on the tissue structure, and a magnetic structure made of a ferrite material for implantation on a tissue structure.

19 Claims, 3 Drawing Sheets

(51) Int. Cl.
　　　*A61N 1/40*　　　(2006.01)
　　　*A61N 2/06*　　　(2006.01)

(56) References Cited

U.S. PATENT DOCUMENTS

| | | | | |
|---|---|---|---|---|
| 5,500,501 | A | * | 3/1996 | Lynum .................. H05H 1/40 |
| | | | | 219/121.48 |
| 5,948,384 | A | | 9/1999 | Filler |
| 2002/0032472 | A1 | | 3/2002 | Zarinetchi et al. |
| 2004/0143300 | A1 | | 7/2004 | Rogers |
| 2008/0319247 | A1 | | 12/2008 | Forbes et al. |
| 2011/0193556 | A1 | * | 8/2011 | Paci .................. G01R 33/07 |
| | | | | 324/251 |
| 2015/0148878 | A1 | | 5/2015 | Yoo et al. |
| 2017/0120065 | A1 | * | 5/2017 | Jiles .................. A61N 2/006 |
| 2018/0028831 | A1 | | 2/2018 | Ron Edoute et al. |
| 2020/0054889 | A1 | * | 2/2020 | Makansi .............. A61N 2/008 |

FOREIGN PATENT DOCUMENTS

| | | |
|---|---|---|
| EP | 0333381 A2 | 9/1989 |
| WO | 96/03112 A1 | 2/1996 |
| WO | 03/022308 A2 | 3/2003 |
| WO | 2004/016316 A1 | 2/2004 |
| WO | 2006116354 A1 | 11/2006 |
| WO | 2007/102375 A1 | 9/2007 |
| WO | 2018071906 A1 | 4/2018 |

\* cited by examiner

METHOD FOR STIMULATING A TISSUE STRUCTURE BY MEANS OF AN ELECTRIC FIELD STRENGTH, A SYSTEM FOR STIMULATING A TISSUE STRUCTURE AND A MAGNETIC STRUCTURE FOR IMPLANTATION ON A TISSUE STRUCTURE

TECHNICAL FIELD

The present disclosure shows concepts for stimulating tissue structures. Embodiments relate to a method for stimulating a tissue structure by means of an electric field strength. Further embodiments relate to a system configured to stimulate a tissue structure by means of an electric field strength, and a magnetic structure for implantation on a tissue structure.

BACKGROUND

For example, human tissue structures, such as nerve cells, may be artificially excited by electrical stimulation. Nerve cells, nerve cords or muscles may, for example, be excited by means of electronic medical technology devices. Nerve cells may be a part of the peripheral nervous system of the human body.

Some systems for simulating peripheral nerves use implants which may consist of complex electronics, an energy storage device and electrodes having connection cables. The electrodes may be used to apply an electric field to the tissue structure, which cause stimulation of the desired nerves or muscles.

The implanted energy storage device is required to supply the implanted electronics with energy and may have a considerable influence on the volume of the implant due to its installation size. It may be necessary to protect the electronics and the energy storage device against moisture that may penetrate the implanted implant. The respective elements therefore are hermetically welded into, e.g., rigid, mostly large and heavy titanium housings. With regard to the energy storage device, for example, further requirements for the technical reliability may be added to ensure tightness, which may vary depending on the requirements for storage capacity.

With such systems, wear and tear may easily occur, e.g., due to electrochemical processes in the human body. In addition, cable connections between the electronics of the implant and the electrodes sometimes have to be attached to the location of stimulation, for example to the tissue structure, if it is not possible to directly place the electronics at the stimulation location due to size and weight.

Disadvantages of implants with integrated electronics may, for example, be possible corrosion of stimulation electrodes, the introduction of charge into the human body, for example through direct current loading during charging of the energy storage device or during stimulation, and high technical requirements for hermetically sealed housings with necessary electrical feedthroughs. Further, failures of the implant or parts of the implant's electronics may occur due to moisture or mechanical effects that may reduce reliability. The implantation of such implants may be complex and costly. Furthermore, high device costs, limited life span of energy storage devices and robustness problems of feedthroughs, cables and electrodes may be disadvantageous, as well as high requirements for electromagnetic compatibility (EMC) or causing interference radiation.

The task of the invention is to provide an improved method for stimulating tissue structures.

Abstract

The task is solved according to the independent patent claims. Advantageous developments are described according to the dependent patent claims, the following description and in the figures.

A method for stimulating a tissue structure by means of an electric field strength is proposed, which comprises generating an electromagnetic alternating field in an environment of the tissue structure and concentrating the electromagnetic alternating field in the tissue structure. The occurrence of direct current loading may be avoided or reduced. Concentrating the electromagnetic alternating field in the tissue structure takes place by means of an implanted magnetic structure within the environment.

According to the method, an electromagnetic alternating field may be generated such that it surrounds the tissue structure and also penetrates the tissue structure and is present within the same. The environment of the tissue structure may, for example, lie within a body with the tissue structure. It is not necessary that a device for generating the electromagnetic alternating field is also positioned inside the body. For example, it is possible to position such a device (such as an electromagnetic coil or an inductive element) outside the body (such as resting on a body surface directly or via an intermediate layer) and direct it towards the body in such a way that an electromagnetic field caused by the device is present within the environment of the tissue structure. The electromagnetic field may, for example, be a time-dependent alternating field or electromagnetic pulses may be generated. An electromagnetic coil may, for example, have a main direction of emission of the electromagnetic field, wherein the main direction of emission may be directed towards the tissue structure in one embodiment of the method.

An electromagnetic field may be generated in the tissue structure and within the environment of the tissue structure by means of a device that is not implanted or does not need to be implanted. To generate the electromagnetic field, the required electronics can, for example, be positioned entirely outside the body and do not need to be implanted in the body. The electromagnetic field has an electric field component that may be used to electrically stimulate or excite the tissue structure. Depending on the selected size of the device (for example a size of the electromagnetic coil) it is possible to generate a field strength of the electromagnetic field and thus of the electric field of different levels. Under certain circumstances, small portable electromagnetic coils, for example, may produce comparatively weak electromagnetic fields of which the electric field component is not readily available in some tissue structures to stimulate the tissue structures.

In the so-called transcranial stimulation to stimulate areas of the brain, large, stationary magnetic coils outside the body may be used, which are placed near the skull and to which correspondingly high currents are applied to generate the required high electromagnetic field strength in the skull, the location of stimulation. The principle of stimulation is based (like that of the proposed stimulation) on the fact that the magnetic field, which varies greatly in time, is connected to an electric field which produces the electric field required for the stimulation or electrostimulation and the associated current required within the skull (and/or within the tissue structure). Large electromagnetic coils may be required to create electric fields with field strengths suitable for stimulating tissue structures in accordance with the transcranial stimulation within the body. In order to generate sufficiently high electric field strengths, a high current is required to be applied to a large electromagnetic coil. Due to the size of the coils required and the high energy needed for the high currents, it is hardly possible to provide small and/or portable devices for stimulation of the tissue structure.

According to the present method, it may be made possible to stimulate tissue structure even with small and/or portable devices without the need to implant electronics into the body. For this purpose, the method according to the invention provides for the concentration of the electromagnetic alternating field in the tissue structure. For example, concentration may take place in a part of the tissue structure (e.g., an area of a nerve cord) to stimulate this part. For example, the area surrounding the tissue structure may comprise an area less than 5 cm (or less than 3 cm) away from the part of the tissue structure to be stimulated. The magnetic structure lies within the area surrounding the tissue structure.

Concentration of the electromagnetic alternating field takes places by means of an implanted magnetic structure positioned within the environment. The magnetic structure may comprise a high magnetic permeability or magnetic conductivity and thus may bundle the field lines of the generated electromagnetic field so that the field strength in the environment of the magnetic structure is higher than in the case in which no magnetic structure was present. For example, the magnetic structure may comprise a metal or a ferromagnetic material (for example an alloy). Thus, an electromagnetic field with an initial, lower field strength may be generated in the environment of the tissue structure and the field strength of the electromagnetic field may be locally concentrated and thus increased by the magnetic structure. Here, the magnetic structure may be positioned directly next to the tissue structure (for example at a minimum distance of less than 0.5 cm) so that the local increase in field strength of the electromagnetic field occurs within the tissue structure. Due to the local concentration of the electromagnetic field, the field strength of the electromagnetic field may be increased by the magnetic structure within the tissue structure to such an extent that it may be used to stimulate the tissue structure.

One advantage of concentrating the electromagnetic field is that it is not necessary to expose the entire body with the tissue structure to a high electromagnetic field strength in order to stimulate the tissue structure. In contrast, it is possible to concentrate or increase the field strength of the electric field used for stimulation exactly at the location where the stimulation of the tissue structure is to take place. Electric currents caused by the electric field flow in a correspondingly locally limited manner in the part of the tissue structure to be stimulated. The high electric field strength required for stimulation may therefore be generated selectively. A further advantage of concentrating the electromagnetic field is that when generating the electromagnetic field large, stationary coils, to which large required currents would have to be applied, may be avoided, something that opens up the possibility of portable electronics. The method makes it possible to reduce the implantation effort for stimulating a tissue structure. In particular, it may be easier to implant the magnetic structure than to implant an implant with electronics, energy storage device and electrodes, particularly as the magnetic structure may be designed comparatively small. The magnetic structure used may also be particularly durable and robust due to its low complexity (e.g., homogeneous solid body, e.g., comprising only one material).

According to a development of the method, a magnetic structure comprising a ferromagnetic and/or ferrimagnetic material is used to increase an electromagnetic field strength on the excitable tissue structure. The ferromagnetic and/or ferrimagnetic material may have non-linear properties (with respect to hysteresis, saturation, etc.). The magnetic structure may comprise a ferrite material, such as a soft-magnetic ferrite material, such as iron, cobalt, manganese, zinc and/or nickel. The magnetic structure may comprise an alloy having at least one of iron, cobalt, manganese, zinc and/or nickel. A permeability number $\mu_r$ of the ferrite material or amorphous metal may, for example, be greater than 80 (or greater than 200, greater than 500, greater than 1000, greater than 10,000 or greater than 100,000) and/or less than 200,000 (or less than 100,000 or less than 10,000). For example, ferrite materials may include a ferrite powder and/or amorphous metals. By using such a magnetic structure, the electromagnetic field may be strongly concentrated due to the high permeability of the magnetic structure. Thus, even with generated electromagnetic fields of a low field strength in the tissue structure, it may still be possible to provide a sufficiently high electric field strength by means of which the tissue structure may be stimulate.

A development of the method provides for the use of a magnetic structure that has a cylindrical shape with its axis pointing towards the tissue structure. The magnetic structure may still have a conical shape. For example, the magnetic structure may decrease (taper) or increase towards the tissue structure. The shape of the magnetic structure may make it possible to achieve a high local focus of the stimulation on a selected tissue structure. For example, a magnetic structure decreasing towards the tissue structure may cause a stronger concentration of the electromagnetic field in the tissue structure. The magnetic structure may be positioned such that it causes an increase in the electromagnetic field strength within the tissue structure. For example, the axis of the magnetic structure may be arranged in parallel to a main direction of emission of a device generating the electromagnetic field.

Optionally, two or more magnetic structures may be provided in the environment of the tissue structure. The two magnetic structures may, for example, be positioned on opposing sides of the tissue structure. This may make it possible to focus and/or concentrate the electric field in the tissue structure between the two magnetic structures.

Optionally, a magnetic structure having a biocompatible cladding layer may be used for the method. This may allow for a medical compatibility of the magnetic structure to be achieved. The biocompatible cladding layer comprises at least one material of hermetically sealed or non-hermetically sealed nature. Hermetically sealed may have a higher density than a non-hermetically sealed material. For example, a hermetically sealed material may be gas-tight and waterproof, for example, a closure that prevents the exchange of air or water. For example, a non-hermetically sealed material may be waterproof. Materials of hermetically sealed nature may be titanium or ceramic, for example. Materials of non-hermetically sealed nature may be silicone or parylene, for example. For example, a thickness of the biocompatible cladding layer may be greater than 0.1 mm (or greater than 0.5 mm, greater than 1 mm or greater than 2 mm) and/or less than 3 mm (or less than 2 mm or less than 1 mm). The biocompatible cladding layer may cause a high degree of compatibility of the magnetic structure for the body in which it is or will be implanted. For example, materials of the magnetic structure may be incompatible with the body, but by using the biocompatible cladding layer, the magnetic structure may still be implanted without any incompatibility problems.

In a development of the method, a magnetic structure is used of which maximum length is less than 5 cm (or less than 4 cm, less than 3 cm, less than 2 cm or less than 1 cm) and/or greater than 0.3 mm (or greater than 0.5 cm, greater than 1 cm or greater than 2 cm). In addition, or alternatively, a magnetic structure is used of which the maximum width is less than 10 mm (or less than 5 mm or less than 3 mm) and/or greater than 1 mm (or greater than 2 mm or greater than 5 mm). For example, the length may be a length and the width may be a diameter of a cylindrical magnetic structure. For example, the size of the magnetic structure may be selected depending on the size of the tissue structure to be stimulated. For example, in an environment of a first tissue structure it may be advantageous to use a longer and narrower magnetic structure, whereas in an environment of a second tissue structure it may be advantageous to use a shorter, wider magnetic structure.

In an embodiment of the method, the concentration of the electromagnetic alternating field causes an increase in a field strength of the electromagnetic alternating field within the tissue structure of at least a factor 5 (or at least a factor 10, at least a factor 20 or at least a factor 50), compared to a case where the magnetic structure is not used or present. This may make it possible to generate an electromagnetic field with a correspondingly lower field strength in order to still be able to cause stimulation by means of the concentrated electromagnetic field. For example, using a larger factor may reduce power requirements for a device for generating the electromagnetic field.

For example, a magnetic field strength concentrated within the tissue structure has a value of at least 100 mT (or at least 500 mT, at least 1000 mT or at least 3000 mT) and/or of at most 10,000 mT (or at most 5,000 mT or at most 3000 mT). For example, the area of the tissue structure where the electromagnetic field is concentrated may comprise a surface of less than 3 mm$^2$ square (or less than 2 mm$^2$ or less than 1 mm$^2$) and/or a surface of more than 2.5 mm$^2$ (or more than 1.5 mm$^2$ or more than 2.5 m$^2$). For example, a minimum field strength within the area may be at least 50% of a maximum field strength within the area. For example, the concentrated magnetic field strength may be provided within a distance of at least 0.1 mm (or at least 0.5 mm or at least 1 cm) and/or of at most 2 cm (or at most 1 cm).

In one embodiment, the magnetic structure is provided less than 2 cm (or less than 1 cm, less than 0.5 cm or less than 0.1 cm) away from the excitable tissue structure and within a body comprising the tissue structure. The range may represent a maximum distance between an edge of the tissue structure and an edge of the magnetic structure.

The provision may include, for example, implanting a magnetic structure prefabricated outside the body comprising the tissue structure. In other words, it may be possible to first fabricate the magnetic structure outside the body and then implant it in the body in the environment of the tissue structure. For example, the prefabricated magnetic structure may be mounted inside the body by means of a biocompatible adhesive in a position where it is possible to concentrate the magnetic field in the tissue structure. The advantage may be that the magnetic structure outside the body is easy to fabricate and, for example, a predetermined shape may be produced precisely.

Alternatively, providing the magnetic structure according to an embodiment of the method comprises injecting ferrite particles and/or ferromagnetic particles into the body. The ferrite particles may be injected at a position next to the tissue structure. In other words, it is possible to fabricate the magnetic structure within the body at the intended position. The ferrite particles are dissolved or suspended in an adhesive when injected (particularly regarding ferrites, ceramics, etc.). The adhesive may be selected such that it cures after a predetermined time after injection, thereby keeping the shape and contour of the magnetic structure stable. For example, the ferrite particles dissolved in the adhesive may be injected by means of a syringe and be precisely positioned so that implantation of a prefabricated magnetic structure may be waived. The ferrite particles may be dissolved in a ferrite emulsion or ferrite suspension for injection. For example, a proportion of ferrite particles in a total mass of the solution comprising the adhesive is higher than 50% (or higher than 70% or higher than 90%) and/or lower than 95% (or lower than 80%). For example, fibrin glue may be used as an adhesive or other biocompatible adhesives may be used. By injecting the ferrite particles and shaping the magnetic structure within the body, it is possible, for example, to provide magnetic structure in hard-to-reach areas of the body.

According to an embodiment of the method, the injected ferrite particles are formed during curing of the adhesive of the injected solution by means of a magnetic field. The magnetic field may be a static or quasi-static magnetic field. For example, the magnetic field may be generated using a coil surrounding the body with the tissue structure and the injected ferrite particles. The ferrite particles still dissolved in the adhesive solution react to the magnetic field generated and change their position depending on the magnetic field. By adjusting the magnetic field, e.g., regulating the magnetic field strength and/or the orientation of the magnetic field, it is possible to shape the ferrite particles such that the magnetic structure results. For example, the magnetic field may be applied until the adhesive has cured and the ferrite particles retain the shape caused by the magnetic field even without the applied magnetic field. The magnetic structure therefore may be formed by means of a magnetic field from the solution of ferrite particles within the body without implanting a prefabricated magnetic structure into the body. This may make it possible to provide the magnetic structure next to the tissue structure while avoiding highly invasive body interventions.

For example, the proposed method may be used to stimulate peripheral nervous structures. In other words, the tissue structure may be a part of a peripheral nervous structure. For example, the tissue structure is a nerve in an arm or a leg of, e.g., a human body. For example, the tissue structure is located in a trunk of a human body. Alternatively, muscle structures may be excited or stimulated. For example, the method for stimulating the tissue structure may be used for non-therapeutic purposes, such as muscle stimulation, e.g. comparable to electromyostimulation (EMS). The method for stimulating the tissue structure may, for example, be used in the field of sports, e.g., to increase muscular performance and support a systematic training process. For example, muscle stimulation may be used to improve or train a rapid strength of the stimulated muscle, which, in the case of random training, is only recruited at maximum loads or movement speeds.

One aspect of the present invention relates to a method for providing a magnetic structure on a tissue structure. The method comprises injecting a mixture comprising at least ferrite particles and bioadhesive into a body comprising the tissue structure. The method further comprises shaping the mixture comprising the ferrite particles and adhesive by means of a magnetic field during a curing process of the adhesive. For example, the magnetic structure provided according to the method may be used to concentrate an electromagnetic field within the tissue structure. For example, the ferrite particles and the bioadhesive may be injected into a region that is less than 1 cm away from the tissue structure. For example, the magnetic field may be used to form a cylindrical and/or conical magnetic structure from the injected ferrite particles and the bioadhesive during curing.

A further aspect of the present invention relates a system for stimulating a tissue structure by means of an electric field strength. The system comprises a portable coil device for generating an electromagnetic alternating field and a magnetic structure implantable on the tissue structure. For example, the magnetic structure may be implanted in a body to concentrate an electromagnetic alternating field generated by the coil device in the tissue structure. For example, the coil device may be positioned outside the body with the tissue structure to stimulate the tissue structure by means of the electromagnetic field.

The system is configured particularly such that, when stimulating the tissue structure, electronics in the portable coil device required to generate the electromagnetic field is located outside a body (e.g., completely or entirely outside a body) with the tissue structure. In other words, when using the system, there is no need to implant electronics, electrodes or electrical cables or lines into the body to operate the system as intended and stimulate the tissue structure. By allowing the system to operate as intended when only (e.g., exclusively) the magnetic structure is implanted in the body, a less invasive intervention in the body (e.g., reduced invasiveness) may be achieved (e.g., compared to systems where electrical connections, electrodes or cables are implanted into the body).

For example, the system is configured without direct contact of electronics or an electrical conductor with the implantable magnetic structure. In particular, there is no need to wrap an electric line around the magnetic structure or to position it on the magnetic structure. It is intended that the system does not have any electronics to be implanted into the body. The magnetic structure may only be of passive design, e.g., essentially ferrite material, adhesive and possibly other connecting materials.

For example, the coil device may comprise full electronics of the system required to generate the electromagnetic field. For example, the coil device has a housing in which a coil is arranged. For example, electrical connections to the coil are arranged exclusively within the housing of the coil device.

The system may enable tissue stimulation with minimized intervention in the body with the tissue structure. For example, only the small magnetic structure has to be implanted into the body without any connection (e.g., electrical cables).

For example, the magnetic structure of the system comprises a maximum length of less than 3 cm and/or a maximum width of less than 1 cm. For example, the magnetic structure comprises a cylindrical and/or conical shape. For example, the magnetic structure is configured as a rigid solid body with a fixed shape. The magnetic structure may, for example, be rod-shaped or lump-shaped. The magnetic structure may comprise a ferromagnetic, a ferrite material or a ferrimagnetic material.

For example, in an operation of the system, a concentration of the electromagnetic alternating field causes an increase in a field strength of the electromagnetic alternating field of at least a factor of 10 in an environment of the magnetic structure (e.g., at a distance of no more than 1 cm away from the magnetic structure, for example in the direction of an axis of the magnetic structure).

For example, in an operation of the system, a magnetic field strength concentrated within an environment of the magnetic structure comprises a value of at least 500 mT. The field strength may have the value of at least 500 mT if the magnetic structure is positioned within a body on a tissue structure.

For example, the magnetic structure of the system is configured to be arranged less than 1 cm away from the excitable tissue structure and within a body comprising the tissue structure.

For example, the portable coil device has a volume of less than 3000 $cm^3$ (or less than 2000 $cm^3$, less than 1000 $cm^3$, or less than mT 500 $cm^3$) and/or a weight of less than 5 kg (or less than 3 kg less than 1 kg or less than 0.5 kg). The coil device may comprise an electrical inductor, control electronics for applying a current to the electrical inductors and an energy storage device. For example, the electrical inductor may be a coil having a diameter of less than 10 cm (or less than 7 cm, less than 5 cm or less than 3 cm). The portable coil device may be designed to be mounted to a body part with the tissue structure. For example, the portable coil device may have a fastening strap. The portability of the coil device makes it possible to stimulate the tissue structure, for example, continuously or at any time without a user of the coil device having to go to a stationary coil device to stimulate the tissue structure.

One aspect of the invention relates to a magnetic structure for implantation on a tissue structure. The magnetic structure comprises at least one ferrite material and has a maximum length of less than 2 cm and/or a maximum width of less than 5 mm. The magnetic structure may have a cylindrical and/or conical shape. For example, the magnetic structure may be round and have a diameter of less than 5 mm or (less than 3 mm or less than 1 mm). For example, the magnetic structure may be bean-shaped or lenticular in shape. For example, the magnetic structure comprises at least a proportion of an adhesive of more than 20%. For example, the adhesive of the magnetic structure may be used to hold ferrite particles, which the magnetic structure comprises, in a predetermined shape of the magnetic structure.

For example, the magnetic structure comprises a conical shape. The magnetic structure may be configured as a rigid solid body. In other words, the magnetic structure may be designed without holes or leadthroughs. The solid body is configured, e.g., free from feedthroughs and/or free from cavities, and/or without any moving components. The magnetic structure may comprise a homogeneous solid body with a fixed shape (e.g., without moving parts).

For example, the magnetic structure comprises a biocompatible cladding layer, the biocompatible cladding layer comprising at least one material of hermetically sealed or non-hermetically sealed nature.

For example, the magnetic structure has a proportion of adhesive of at least 20% and/or a proportion of ferrite material of at least 50%.

One aspect of the present disclosure relates to a magnetic structure for implantation on a tissue structure, e.g., next to a tissue structure. The magnetic structure comprises at least one ferrite material, wherein the magnetic structure comprises a maximum length of less than 3 cm and/or a maximum width of less than 1 cm and wherein the magnetic structure is bean-shaped or lenticular in shape.

Another aspect concerns a suspension for injection into a body to fabricate a magnetic structure within the body. For example, the suspension comprises an adhesive and ferrite particles dissolved in the adhesive. For example, the suspension is a solution comprising adhesive, ferrite particles and solvents. The adhesive may be a bioadhesive.

The suspension is configured, for example, for injection by means of a syringe. In other words, the suspension may be liquid enough to be injected into a body by means of a syringe, for example. The suspension may, for example, cure in the body so that a fixed, rigid magnetic structure may be formed. For example, simple geometries, e.g., solid bodies without feedthroughs or cavities, may be formed by injecting the suspension.

For example, the proportion of ferrite particles in the suspension is at least 50% (or at least 70%). The proportion of adhesive may be more than 20% (or more than 30%).

Further aspects of the method for providing the magnetic structure, the system for stimulating a tissue structure and the magnetic structure relate to embodiments that have already been shown in connection with the method for stimulating a tissue structure. Therefore, we will refrain from showing these features of the method for providing the magnetic structure, the system for stimulating a tissue structure and the magnetic structure separately once again.

One aspect relates to a method for generating a stimulation signal for at least partially avoiding direct current loading and for reducing interference radiation (EMC) with minimalist implant electronics.

BRIEF DESCRIPTION OF THE FIGURES

Some examples of devices and/or methods will be described in the following by way of example only and with reference to the accompanying figures, in which.

DESCRIPTION

Various examples will now be described in more detail with reference to the accompanying figures in which some examples are illustrated. The thickness of lines, layers and/or areas in the figures may also be exaggerated for clarification.

Accordingly, while further examples are capable of various modifications and alternative forms, some particular examples thereof are shown in the figures and will subsequently be described in detail. However, this detailed description does not limit further examples to the particular forms described. Further embodiments may cover all modifications, equivalents, and alternatives falling within the scope of the disclosure. Throughout the description of the figures, same reference numerals refer to same or similar elements, which, when compared, may be identical or implemented in a modified form while providing the same or a similar function.

It will be understood that when an element is referred to as being "connected" or "coupled" to another element, the elements may be directly connected or coupled via one or more intervening elements. When two elements A and B are combined using an 'or', this is to be understood as disclosing all possible combinations, i.e. only A, only B as well as A and B. An alternative wording for the same combinations is "at least one of A and B". The same applies to combinations of more than two elements.

The terminology used herein to describe certain examples should not be restrictive of further examples. If a singular form, such as "a", "an" and "the" is used and the use of only a single element is not defined as mandatory either explicitly or implicitly, further examples may also use plural elements to implement the same function. Likewise, when a function is subsequently described as being implemented using several elements, further examples may implement the same functionality using a single element or a single processing entity. It will be further understood that the terms "comprises", "comprising", "includes" and/or "including," when used, specify the presence of the stated features, integers, steps, operations, processes, elements, components and/or any group of the same, but do not preclude the presence or addition of one or more other features, integers, steps, operations, processes, elements, components and/or any group thereof.

Unless defined otherwise, all terms (including technical and scientific terms) are used herein in their ordinary meaning of the art to which the examples belong.

Figure 1:
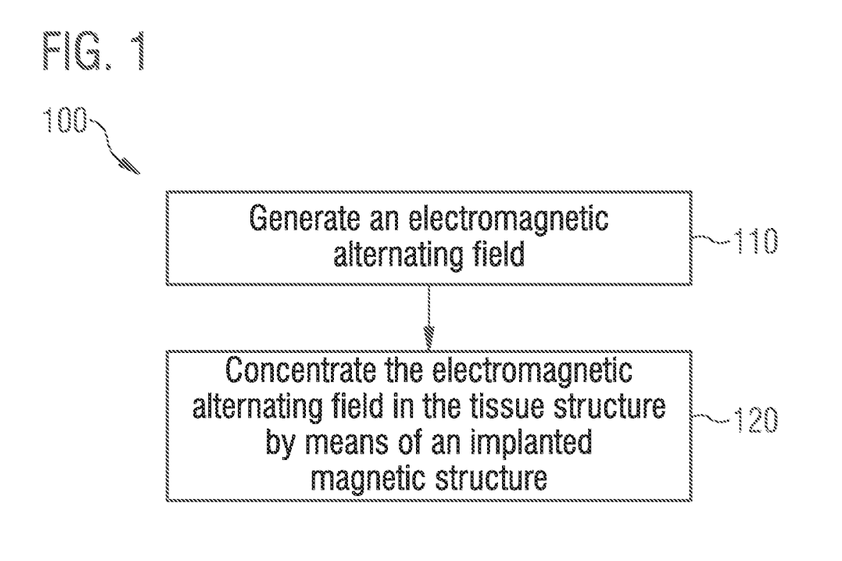
FIG. 1 shows an example of a method for stimulating a tissue structure.

FIG. 1 shows a flowchart of an exemplary method 100 for stimulating a tissue structure. The method 100 comprises generating 110 an electromagnetic alternating field in an environment of the tissue structure. The method 100 further comprises concentrating 120 the electromagnetic alternating field in the tissue structure by means of an implanted magnetic structure.

The method 100 is suitable, for example, for stimulating a tissue structure within a body, wherein an electronic device outside the body may be used for stimulation. For example, a portable coil device may be used to generate an electromagnetic field outside the body, which is directed towards the body (for example by appropriate positioning of the portable coil device) in such a way that an electromagnetic alternating field is generated 110 in the environment of the tissue structure.

As the electromagnetic alternating field, which may be produced by a portable coil device, may possibly have an electric field strength that is too low to directly stimulate the tissue structure, the implanted magnetic structure is used according to the method 100 to concentrate 120 the electromagnetic field. The magnetic structure may be implanted in the environment of the tissue structure so that it concentrates the electromagnetic field generated by the external coil device within the tissue structure. In other words, the magnetic structure may be described as a magnetic field concentrator. By concentrating 120 the electromagnetic field, the field strength of the electric field component within the tissue structure may be increased to a value at which the tissue structure may be electrically stimulated.

Providing the implanted magnetic structure according to method 100 makes it possible to use portable coil devices with coils of a small size to stimulate the tissue structure. The coils of the portable coil device require an energy supply that may be provided, for example, by a battery or an energy storage device of the portable coil device. In order to provide an electric field strength in the tissue structure despite the small coil size, which enables the tissue structure to be stimulated, the magnetic field concentrator in the form of the implanted magnetic structure is used. In contrast to other systems (e.g., systems with electrodes), the magnetic field concentrator allows for the energy required for stimulation to be concentrated locally in a targeted manner, so that the total energy required may be reduced by efficient use and therefore may be provided by a portable device (e.g., battery operated).

The method 100 allows for only the magnetic structure having to be implanted or incorporated into the body to stimulate the tissue structure, whereas any and all electronic devices required for stimulation (for example to generate the electromagnetic field or the electric field) may be operated outside the body with the tissue structure. This may reduce an implantation effort.

Figure 2:
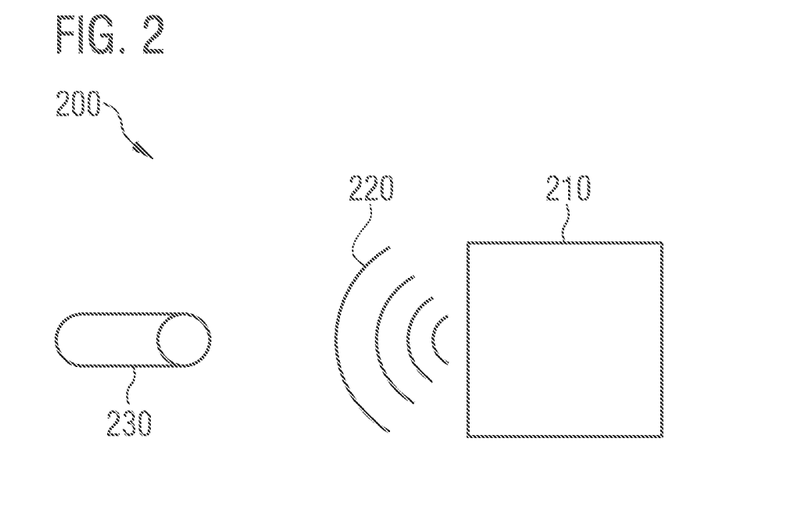
FIG. 2 shows an example of a system for stimulating a tissue structure.

FIG. 2 shows an exemplary system 200 for stimulating a tissue structure (not illustrated). The system 200 comprises a portable coil device 210 for generating an electromagnetic alternating field 220. The system 200 also comprises a magnetic structure 230 that may be implanted on the tissue structure. For example, the implantable magnetic structure may be implanted into a body with the tissue structure.

Figure 3:
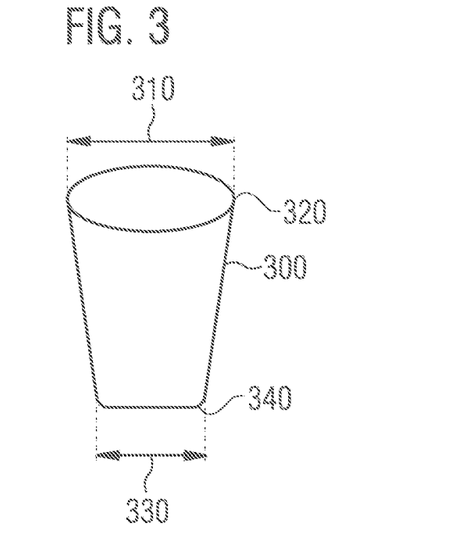
FIG. 3 shows an exemplary magnetic structure for implantation on a tissue structure.

FIG. 3 shows an exemplary magnetic structure 300 for implantation on a tissue structure. The magnetic structure 300 has a conical shape. A first diameter 310 on a first side 320 of the magnetic structure 300 is larger than a second diameter 330 on a second side 340 of the magnetic structure 300. For example, the first diameter 310 is more than 20% (or more than 40%, more than 60%, more than 100% or more than 200%) and/or less than 300% (or less than 200% or less than 100% or less than 50%) larger than the second diameter 330. For example, all edges of the conical shape are rounded.

Figure 4:
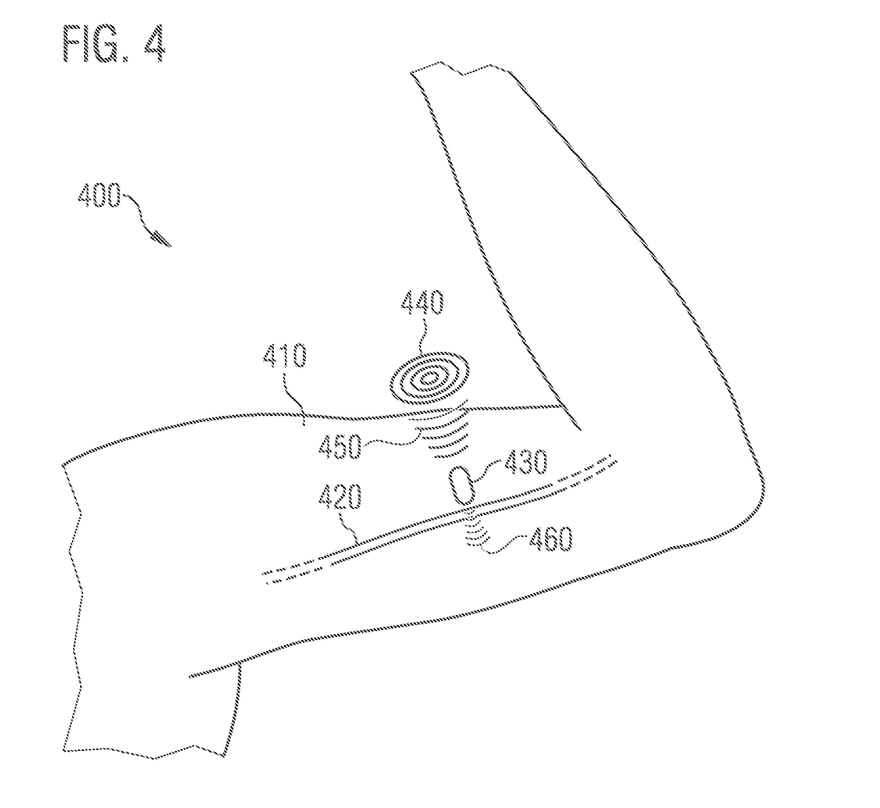
FIG. 4 shows an example of stimulation of a peripheral nerve cord.

FIG. 4 shows an example 400 of a stimulation of peripheral nerves. Here an upper arm 410 is shown with a section of nerve cord 420. A magnetic structure 430 is provided in the vicinity or environment of the nerve cord 420. The magnetic structure for 130 is, for example, provided by implantation or injection of ferrite particles. A portable coil device 440 (only illustrated schematically and not completely) generates an electromagnetic alternating field 450 which is directed towards the magnetic structure 430. The portable coil device 440, for example, comprises a housing with a maximum height of 5 cm (i.e., the portable coil device does not protrude more than 5 cm from the upper arm), so that it may be worn under an item of clothing, for example. The electromagnetic alternating field 450 is provided by the alignment of the coil of the coil device 440 in such a way that it is present in the environment of the nerve cord 420 and the magnetic structure 430.

The magnetic structure 430 concentrates the electromagnetic alternating field 450 to a concentrated electromagnetic field 460 within the nerve cord 420. The magnetic structure 430 bundles the field lines of the electromagnetic alternating field 450 to increase the field strength of the electric field in the nerve cord 420 to stimulate the nerve cord 420.

Figure 5:
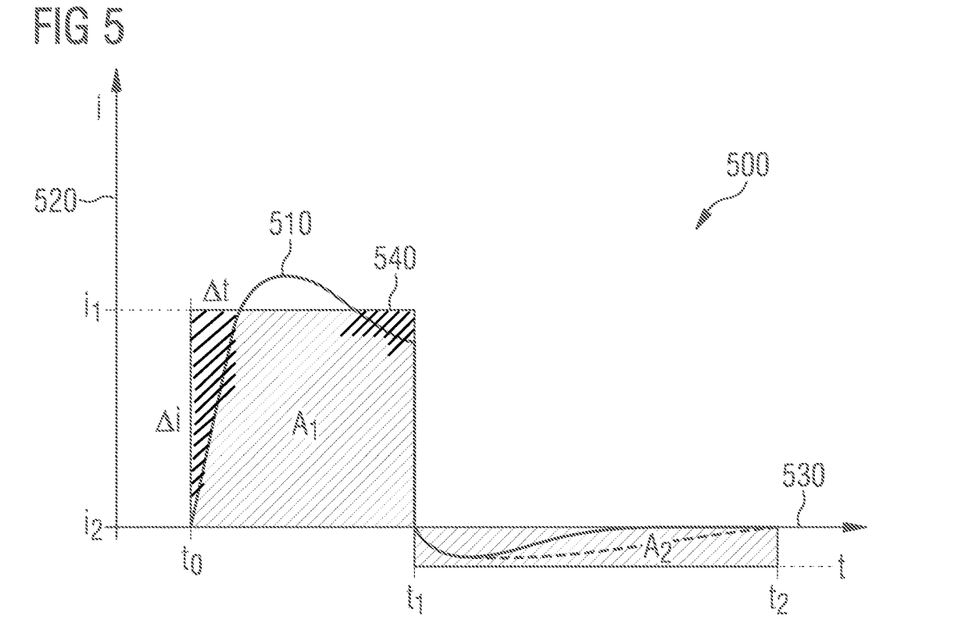
FIG. 5 shows an example of a first stimulation signal.

FIG. 5 shows an example 500 of a first stimulation signal 510. A current 520 of the first stimulation signal 510 is plotted over a time axis 530. The stimulation signal 510 may be generated according to a method for generating a stimulation signal to avoid direct current loading and reduce interference radiation (EMC) with minimalist implant electronics.

An idealized stimulation pulse 540 (rectangular pulse in FIG. 5 comprising the shown hatched areas A1 and A2) may have areas A1, A2 of equal size in order to avoid direct current loading (charge introduction). With conventional implants, this may be ensured by electronics that are able to generate a course of the stimulation pulse as shown in FIG. 5. According to the disclosed invention, the pulse shape shown may be generated directly by a magnetic field or also by means of a coil (e.g., with non-linear inductor), both by effect of the law of induction. If a coil is used in the implant, conventional electrodes may be used. The advantage is the provision of a transitional/intermediate solution between conventional concepts for stimulation and inventive concepts for stimulation for the complete electrode- and electronics-free (with respect to the implant) inventive solution.

Figure 6:
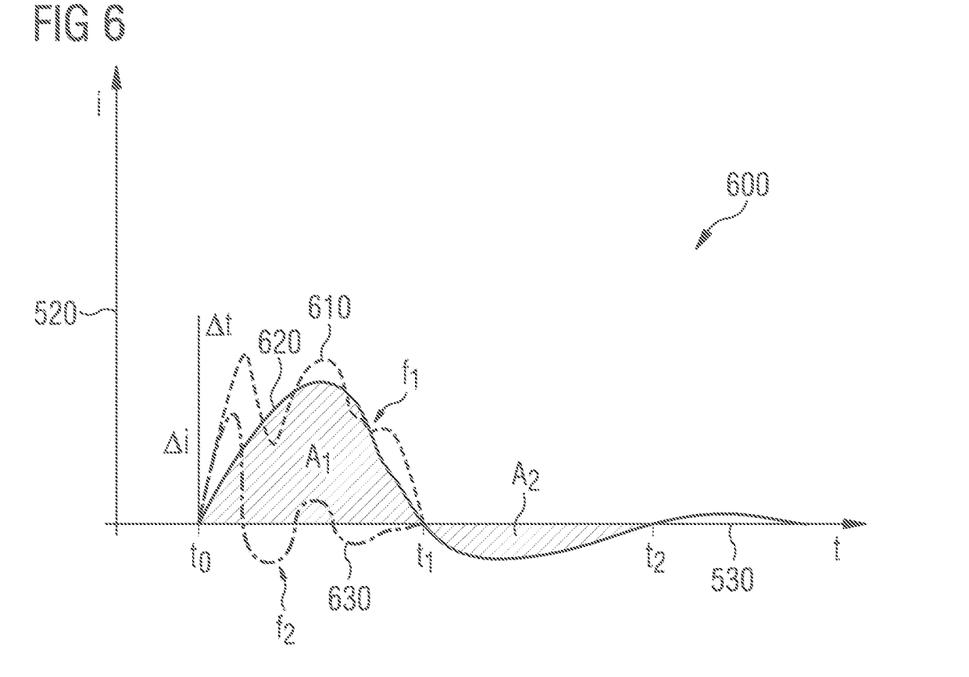
FIG. 6 shows an example of a second stimulation signal.

FIG. 6 is an example 600 of a second stimulation signal 610. The stimulation signal 610 may be shaped by superimposing two signals 620, 630 with different frequencies. A so-called "aperiodic borderline case" of an excited oscillation may preferably result for the lower frequency (kHz range). The superimposition of these two frequencies then results in a signal course of the second stimulation signal 610 corresponding to the dotted line in FIG. 6. This is one way of ensuring the rate of current rise required for stimulation $\Delta i/\Delta t$ as shown in FIG. 5. On the one hand, the superimposition may be achieved by electronics outside the body (for example in a coil device according to the invention) or by exploiting non-linear properties (hysteresis, saturation) of ferromagnetic (or ferri-) magnetic materials in the magnetic structure.

The invention enables wireless, targeted electrostimulation that manages without electrodes, cables, electronics or energy storage devices. The invasiveness of the proposed concept may be reduced to a minimum by forming implant bodies (e.g., magnetic structure) in the human body. The invention makes it possible to provide portable devices (portable in terms of size, weight, power supply). Numerous applications thus may be carried out at any time by stimulating tissue structures, e.g., alleviating the symptoms of pain, migraine or high blood pressure. In combination with a small, easily implantable magnetic structure, localized stimulation of excitable tissue is made possible. In addition, the stimulation of the central nerves and muscles may be possible, as the required electric field strength, which is different for the two cases, may, for example, be provided by the design of the coil device and/or the magnetic structure.

According to the concepts presented, for example, the entire "intelligence" (e.g., electronic components, energy storage device, control) of the stimulation system is provided in an externally worn module that provides the energy supply and control for stimulation, while the implant itself is designed as minimalist as possible. Embodiments are based on the application of electromagnetic fields in interaction with implanted ferrite particles (e.g., no nanoparticles) and/or prefabricated ferrite bodies, which concentrate the externally introduced electromagnetic energy in such a way that locally limited action potentials may be triggered or other mechanisms of action may be used.

Systems with magnetic coils placed outside the body and with implanted magnetic field concentrators inside the body may result in advantages: No electrodes are required, therefore no corrosion of stimulation electrodes may occur; charge introduction into the human body (direct current loading) may be avoided; no hermetically sealed housings with necessary electrical feedthroughs are necessary; as the field strength or magnetic flux density per penetrated surface is decisive for the intended effect, and as there is also a small spatial extent (nerves), the desired effect of an electrostimulation may be achieved with less energy input and therefore with smaller external coils and lower currents; the magnetic field concentrators allow for local focusing of the stimulation. Tissue structures surrounding the location of the desired stimulation may be left unaffected.

Further examples describe further aspects of the present disclosure. A first example relates to a method for stimulating a tissue structure by means of an electric field strength, comprising: generating an electromagnetic alternating field in an environment of the tissue structure; and concentrating the electromagnetic alternating field in the tissue structure by means of an implanted magnetic structure within the environment.

A second example relates to a method of example 1, wherein the magnetic structure comprises a ferromagnetic or ferrimagnetic material to increase an electromagnetic field strength on the excitable tissue structure, wherein the material may comprise non-linear properties.

A third example relates to a method of any of the preceding examples 1 or 2, wherein the magnetic structure comprises a cylindrical shape with its axis pointing towards a tissue structure.

A fourth example relates to a method of any of the preceding examples 1 to 3, wherein the magnetic structure comprises a biocompatible cladding layer, the biocompatible cladding layer comprising at least one material of hermetically sealed or non-hermetically sealed nature.

A fifth example relates to a method of any of the preceding examples 1 to 4, wherein a maximum length of the magnetic structure is less than 3 cm and/or a maximum width of the magnetic structure is less than 1 cm.

A sixth example relates to a method of any of the preceding examples 1 to 5, wherein concentrating the electromagnetic alternating field causes a field strength of the electromagnetic alternating field to increase by at least a factor of 10 in the tissue structure.

A seventh example relates to a method of any of the preceding examples 1 to 6, wherein a magnetic field strength concentrated within the tissue structure comprises a value of at least 500 mT.

An eighth example relates to a method of any of the preceding examples 1 to 7, further comprising:
providing the magnetic structure, less than 1 cm away from the excitable tissue structure and within a body comprising the tissue structure.

A ninth example relates to a method of example 8, wherein providing comprising implanting a magnetic structure pre-fabricated outside the body comprising the tissue structure.

A tenth example relates to a method of example 8, wherein providing comprising injecting ferrite particles dissolved in an adhesive into the body.

An eleventh example relates to a method of example 10, wherein the injected ferrite particles are formed during a curing process of the injected solution by means of a magnetic field.

A twelfth example relates to a method of any of the preceding examples 1 to 11, wherein the tissue structure is a peripheral nervous structure.

A thirteenth example relates to a method for providing a magnetic structure on a tissue structure, the method comprising: injecting a mixture comprising at least ferrite particles and bioadhesive into a body comprising the tissue structure; and shaping the mixture comprising the ferrite particles and adhesive by means of a magnetic field during a curing process of the adhesive.

A fourteenth example relates to a system for stimulating a tissue structure by means of an electric field strength, comprising: a portable coil device for generating an electromagnetic alternating field; and a magnetic structure implantable on the tissue structure.

A fifteenth example relates to a system of example 14, wherein the portable coil device comprises a volume of less than 2000 $cm^3$ and/or a weight of less than 3 kg.

A sixteenth example relates to a magnetic structure for implantation on a tissue structure, the magnetic structure comprising at least one ferrite material, wherein the magnetic structure comprises a maximum length of less than 3 cm and/or a maximum width of less than 1 cm and wherein the magnetic structure comprises a cylindrical shape.

A further example relates to a method for generating a stimulation signal for stimulating a tissue structure, wherein, due to a signal form of the stimulation signal, of which the positive maximum value is greater in magnitude than its negative maximum value and of which the integral value in terms of magnitude comprises less than 5% of its maximum magnitude, direct current loading and interference radiation are reduced.

The aspects and features mentioned and described together with one or more of the previously detailed examples and figures may as well be combined with one or more of the other examples in order to replace a like feature of the other example or in order to additionally introduce the feature to the other example.

Examples may further be or relate to a computer program having a program code for performing one or more of the above methods, when the computer program is executed on a computer or processor. Steps, operations or processes of various above-described methods may be performed by programmed computers or processors. Examples may also cover program storage devices such as digital data storage media, which are machine, processor or computer readable and encode machine-executable, processor-executable or computer-executable programs of instructions. The instructions perform or cause performing some or all of the acts of the above-described methods. The program storage devices may comprise or be, for instance, digital memories, magnetic storage media such as magnetic disks and magnetic tapes, hard drives, or optically readable digital data storage media. Further examples may also cover computers, processors or control units programmed to perform the acts of the above-described methods or (field) programmable logic arrays ((F)PLAs) or (field) programmable gate arrays ((F)PGAs), programmed to perform the acts of the above-described methods.

The description and drawings merely illustrate the principles of the disclosure. Furthermore, all examples recited herein are principally intended expressly to be only for pedagogical purposes to aid the reader in understanding the principles of the disclosure and the concepts contributed by the inventor(s) to furthering the art. All statements herein reciting principles, aspects, and examples of the disclosure, as well as specific examples thereof, include equivalents thereof.

A functional block denoted as "means for . . . " performing a certain function may refer to a circuit that is configured to perform a certain function. Hence, a "means for s.th." may be implemented as a "means configured to or suited for s.th.", such as a device or a circuit configured to or suited for the respective task.

Functions of various elements shown in the Figures, including any functional blocks labeled as "means", "means for providing a signal", "means for generating a signal.", etc., may be implemented in the form of dedicated hardware, such as "a signal provider", "a signal processing unit", "a processor", "a controller", etc. as well as hardware capable of executing software in association with appropriate software. When provided by a processor, the functions may be provided by a single dedicated processor, by a single shared processor, or by a plurality of individual processors, some of which or all of which may be shared. However, the term "processor" or "controller" is by far not limited to hardware exclusively capable of executing software, but may include digital signal processor (DSP) hardware, a network processor, an application specific integrated circuit (ASIC), a field programmable gate set (FPGA), read only memory (ROM) for storing software, random access memory (RAM), and non-volatile storage. Other hardware, conventional and/or custom, may also be included.

A block diagram may, for instance, illustrate a rough circuit diagram implementing the principles of the disclosure. Similarly, a flow chart, a flow diagram, a state transition diagram, a pseudo code, and the like may represent various processes, operations or steps, which may, for instance, be substantially represented in computer readable medium and so executed by a computer or processor, whether or not such computer or processor is explicitly shown. Methods disclosed in the specification or in the claims may be implemented by a device having means for performing each of the respective acts of these methods.

It is to be understood that the disclosure of multiple acts, processes, operations, steps or functions disclosed in the specification or claims may not be construed as to be within the specific order, unless explicitly or implicitly stated otherwise, for instance for technical reasons. Therefore, the disclosure of multiple acts or functions will not limit these to a particular order unless such acts or functions are not interchangeable for technical reasons. Furthermore, in some examples a single act, function, process, operation or step may include or may be broken into multiple sub-acts, -functions, -processes, -operations or -steps, respectively. Such sub acts may be included and part of the disclosure of this single act unless explicitly excluded.

Furthermore, the following claims are hereby incorporated into the detailed description, where each claim may stand on its own as a separate example. While each claim may stand on its own as a separate example, it is to be noted that—although a dependent claim may refer in the claims to a specific combination with one or more other claims—other examples may also include a combination of the dependent claim with the subject matter of each other dependent or independent claim. Such combinations are explicitly proposed herein unless it is stated that a specific combination is not intended. Furthermore, it is intended to also include features of a claim to any other independent claim even if this claim is not directly made dependent to the independent claim.

The invention claimed is:

1. A system for stimulating a tissue structure by means of an electric field strength, comprising:
    a portable coil device for generating an electromagnetic alternating field; and
    a magnetic structure implantable on the tissue structure,
    wherein, in operation of the system, a magnetic field strength concentrated within an environment of the magnetic structure comprises a value of at least 500 mT, and
    wherein, in operation of the system, concentrating the electromagnetic alternating field causes a field strength of the electromagnetic alternating field to increase by at least a factor of 10 in the environment of the magnetic structure.

2. The system of claim 1, wherein the system is configured such that, when stimulating the tissue structure, electronics in the portable coil device required to generate the electromagnetic alternating field are located entirely outside a body with the tissue structure.

3. The system of claim 1, wherein the system for stimulating the tissue structure is configured without any structural connection between electronics or an electrical conductor and the implantable magnetic structure.

4. The system of claim 1,
    wherein the system does not comprise any electronics, electrodes or electrical conductors to be implanted in a body, and/or
    wherein the portable coil device comprises full electronics of the system to generate the electromagnetic alternating field.

5. The system of claim 1, wherein the magnetic structure comprises a maximum length of less than 3 cm and/or a maximum width of less than 1 cm.

6. The system of claim 1,
    wherein the magnetic structure comprises a cylindrical and/or conical shape, and/or
    wherein the magnetic structure is configured as a rigid solid body with a fixed shape.

7. The system of claim 1, wherein the magnetic structure comprises a ferromagnetic, a ferrite material or a ferrimagnetic material.

8. The system of claim 1, wherein the magnetic structure comprises a proportion of an adhesive of more than 20%.

9. The system of claim 1, wherein the magnetic structure comprises a biocompatible cladding layer, the biocompatible cladding layer comprising at least one material of hermetically sealed or non-hermetically sealed nature.

10. The system of claim 1, wherein the magnetic structure is configured to be arranged less than 1 cm away from a tissue structure to be excited and within a body comprising the tissue structure.

11. The system of claim 1, wherein the portable coil device comprises a volume of less than 2000 $cm^3$ and/or a weight of less than 3 kg.

12. A magnetic structure for implantation on a tissue structure, the magnetic structure comprising:
    at least one ferrite material,
    wherein the magnetic structure comprises a maximum length of more than 1 cm and less than 3 cm and/or a maximum width of more than 1 mm and less than 1 cm, and
    wherein the magnetic structure comprises a cylindrical shape,
    wherein, when exposed to an electromagnetic alternating field, a magnetic field strength concentrated within an environment of the magnetic structure comprises a value of at least 500 mT and the magnetic structure concentrates the electromagnetic alternating field to cause a field strength of the electromagnetic alternating field in the environment of the magnetic structure to increase by at least a factor of 10.

13. The magnetic structure of claim 12, wherein the magnetic structure comprises a conical shape.

14. The magnetic structure of claim 12,
    wherein the magnetic structure is configured as a rigid solid body.

15. The magnetic structure of claim 14, wherein the solid body is configured free from feedthroughs and/or free from cavities, and/or is configured without any moving components.

16. A magnetic structure for implantation on a tissue structure, the magnetic structure comprising:
- at least one ferrite material, wherein the magnetic structure comprises a maximum length of less than 3 cm and/or a maximum width of less than 1 cm, wherein the magnetic structure is bean-shaped or lenticular in shape,
- wherein, when exposed to an electromagnetic alternating field, a magnetic field strength concentrated within an environment of the magnetic structure comprises a value of at least 500mT and the magnetic structure concentrates the electromagnetic alternating field to cause a field strength of the electromagnetic alternating field in the environment of the magnetic structure to increase by at least a factor of 10.

17. A suspension for injection into a body to fabricate a magnetic structure within the body, the suspension comprising:
- an adhesive; and
- ferrite particles dissolved in the adhesive,
- wherein the proportion of the ferrite particles in the suspension is at least 50%
- wherein, when fabricated and exposed to an electromagnetic alternating field, a magnetic field strength concentrated within an environment of the magnetic structure comprises a value of at least 500mT and the magnetic structure concentrates the electromagnetic alternating field to cause a field strength of the electromagnetic alternating field in the environment of the magnetic structure to increase by at least a factor of 10.

18. The suspension of claim 17, wherein the suspension is a bioadhesive.

19. A system for stimulating a tissue structure by means of an electric field strength, comprising:
- a portable coil device for generating an electromagnetic alternating field; and
- a magnetic structure implantable on the tissue structure,
- wherein the magnetic structure comprises a ferromagnetic, a ferrite material or a ferrimagnetic material, wherein the material comprises non-linear properties, and
- wherein, in operation of the system, a magnetic field strength concentrated within an environment of the magnetic structure comprises a value of at least 500 mT and the magnetic structure concentrates the electromagnetic alternating field to cause a field strength of the electromagnetic alternating field in the environment of the magnetic structure to increase by at least a factor of 10.

* * * * *